(12) United States Patent
Feng et al.

(10) Patent No.: US 9,453,829 B2
(45) Date of Patent: Sep. 27, 2016

(54) SOIL PROPERTY TEST DEVICE

(71) Applicant: SHIJIAZHUANG TIEDAO UNIVERSITY, Shijiazhuang, Hebei (CN)

(72) Inventors: Huaiping Feng, Shijiazhuang (CN); Jianmei Chang, Shijiazhuang (CN); Tielin Li, Shijiazhuang (CN); Yanjie Lin, Shijiazhuang (CN); Chaoliang Ye, Shijiazhuang (CN); Tianliang Wang, Shijiazhuang (CN); Zhipeng Wang, Shijiazhuang (CN); Yafei Liu, Shijiazhuang (CN)

(73) Assignee: SHIJIAZHUANG TIEDAO UNIVERSITY, Shijiazhuang (CN)

( * ) Notice: Subject to any disclaimer, the term of this patent is extended or adjusted under 35 U.S.C. 154(b) by 0 days.

(21) Appl. No.: 14/768,621

(22) PCT Filed: Dec. 22, 2014

(86) PCT No.: PCT/CN2014/094458
§ 371 (c)(1),
(2) Date: Aug. 18, 2015

(87) PCT Pub. No.: WO2015/096672
PCT Pub. Date: Jul. 2, 2015

(65) Prior Publication Data
US 2015/0377853 A1 Dec. 31, 2015

(30) Foreign Application Priority Data

Dec. 23, 2013 (CN) .......................... 2013 1 0716611
Dec. 23, 2013 (CN) .......................... 2013 1 0716893

(51) Int. Cl.
*G01N 33/24* (2006.01)
*G01N 15/08* (2006.01)
*G01N 1/28* (2006.01)

(52) U.S. Cl.
CPC ................ *G01N 33/24* (2013.01); *G01N 1/28* (2013.01); *G01N 15/08* (2013.01); *G01N 15/0806* (2013.01)

(58) Field of Classification Search
CPC .... G01N 33/24; G01N 33/246; G01N 15/08; G01N 15/0806; G01N 15/088; G01N 2015/0866; G01N 2015/0873
USPC .......................................... 73/38, 865.6, 863
See application file for complete search history.

(56) References Cited

U.S. PATENT DOCUMENTS 5,036,193 A * 7/1991 Davis, Jr. ............. G01N 15/088
250/255
6,718,835 B2 * 4/2004 Wang ..................... E02D 1/027
73/38

(Continued)

FOREIGN PATENT DOCUMENTS

CN  101672761 A  3/2010
CN  101915718 A  12/2010

(Continued)

OTHER PUBLICATIONS

Mar. 24, 2015 International Search Report issued in International Patent Application No. PCT/CN2014/094458.

*Primary Examiner* — Peter Macchiarolo
*Assistant Examiner* — Nathaniel Kolb
(74) *Attorney, Agent, or Firm* — Oliff PLC

(57) ABSTRACT

A test device including a closeable cavity and a water flow groove with a water transmission channel existing between the water flow groove and the internal part of the cavity. The water flow groove includes a water inlet and a water outlet with the depth of the water inlet being greater than the depth of the water outlet. Simultaneously, side lead-in pipe of drain pipe and elbow pipe on side wall of water inlet pipe are consistent with height of top surface of the ceramic plate, making hydraulic pressure of tested soil sample being zero during dehydrating and soaking process capable of ensuring accuracy of test result. A necking design is applied to reduce water evaporation in the drainage pipe and lower the test errors. Side lead-in pipe is connected with drainage pipe for smoothly draining water and also can prevent air reversely flowing and entering into the base.

18 Claims, 5 Drawing Sheets

(56) References Cited

U.S. PATENT DOCUMENTS

| | | |
|---|---|---|
| 8,800,353 B2 | 8/2014 | Ng |
| 2009/0099793 A1 | 4/2009 | Rosati et al. |
| 2012/0060588 A1 | 3/2012 | Ng |

FOREIGN PATENT DOCUMENTS

| | | | |
|---|---|---|---|
| CN | 202141719 U | | 2/2012 |
| CN | 102445528 A | | 5/2012 |
| CN | 202599945 U | | 12/2012 |
| CN | 103235107 A | | 8/2013 |
| CN | 203324134 U | * | 12/2013 |
| CN | 103743882 A | | 4/2014 |
| CN | 103743883 A | | 4/2014 |
| JP | 20051291862 A | | 10/2005 |
| KR | 100486837 B1 | | 4/2005 |

\* cited by examiner

SOIL PROPERTY TEST DEVICE

PRIORITY

The present invention claims the priority of the Chinese patent application No. CN201310716611.1 filed on Dec. 23, 2013 and entitled "A Device for Measuring the Air Entry Value of Unsaturated Soil", and the Chinese patent application No. CN201310716893.5 filed on Dec. 23, 2013 and entitled "A Device and Method for Measuring the Hysteresis Curve of Unsaturated Soil". All of their documents are incorporated into the present invention by references.

TECHNICAL FIELD

The present invention relates to a test device, in particular a device applicable to testing the engineering properties of unsaturated soil, and belongs to the technical field of geotechnical engineering.

BACKGROUND

It is generally believed that soil is composed of solid phase (soil particles), liquid phase (pore water) and gas phase (gas contained in soil). When the interspace of soil particles are completely filled with liquid phase, the soil is defined as saturated soil. Otherwise, when the interspace in soil is filled with the water and air, that is, when the saturation degree is lower than 100%, the soil is defined as unsaturated soil.

The geotechnical engineering usually involves the problems about engineering properties of unsaturated soil. Study on the engineering properties of unsaturated soil should start with the soil water characteristics of unsaturated soil. No matter in the application field or research field, providing accurate soil water characteristics of unsaturated soil is of great importance for the geotechnical engineering technology. The soil water characteristic curve of unsaturated soil is used to reflect the relationship between the matrix suction and the volumetric water content, which has important significance for determining the shear strength, volume change and permeability coefficient of unsaturated soil. The soil water characteristic curve has significant hysteresis phenomenon, i.e., the dehydration curve shall be higher than the soaking curve, and both form a hysteresis loop. This means that under the same net pressure and matrix suction, soil may have different saturation degrees, and may show different shear strengths and permeability coefficients. Soil hysteresis problems extensively exist in the engineering practice. For example, affected by the water level change in the reservoir area, side slope will be bound to experience repeated dehydration-soaking-dehydration process. Therefore, accurately testing the hysteresis phenomenon of unsaturated soil has very important significance for study on the unsaturated soil theory and the engineering design.

The air entry value (AEV) of unsaturated soil means the matrix suction required to produce unsaturation in the maximum pores within the soil mass, and is an important parameter for dividing saturated state or unsaturated state of the soil mass. Precision of AEV has great influence on the dehumidification scan line with the starting point in the high saturation area, and also plays a crucial role in capillary block impervious layer design of the engineering application. Therefore, accurate determination of the AEV of materials becomes a very important work in the hydraulic properties test of unsaturated soil.

Pressure plate apparatus is one of the basic devices to determine the soil water characteristic curve of unsaturated soil. The commonly used test device includes: Fredlund SWCC pressure plate apparatus, Geoexpert pressure plate apparatus and a soil water characteristic curve tester provided in Chinese utility model patent No. 201120271620.0. According to these test methods, because of the migration effect in the discharge water test, bubbles are generated below the ceramic plate, and are collected in the drain pipe. The volume of the bubbles is easy to be mistaken for the discharge water amount, thereby affecting the accuracy of the water discharge test. At present, bubbles are usually discharged by means of repeated washing to solve this problem, which not only causes more cumbersome operation steps, but also increases the difficulty of the test work. Therefore, developing a test device capable of automatically discharging bubbles from the base has important significance for accurate test of the soil water characteristic curve.

Besides, at present, in the process of air entry value determination of unsaturated soil with the pressure plate apparatus based on the axis parallel translation technique, it is generally assumed that the water pressure below the soil mass is zero, that is, the applied pressure is the matrix suction in soil. However, the drainage water measuring tube of the above apparatus is usually fixed on the bench of the apparatus, and the initial liquid level in the measuring tube is generally 20~30 cm higher than the soil sample. Actual water pressure of 2~3 KPa will be produced below soil, and will be improved with the rise of the water level in the drainage water measuring tube. This changing water pressure often existing in soil has very significant influence on the test precision of air entry value of unsaturated soil, as well as the hysteresis curve test. Specifically, the above test apparatus has three defects as follows:

1. At low matrix suction, due to reduced air pressure and water pressure effect in the water inlet in the soaking experiment, excess water will be collected on the ceramic plate, and there will be the phenomenon such as macerated soil samples, resulting in water inflow test error.

2. It is impossible to accurately test the air entry value. The air entry value of the soil sample is generally 5~20 KPa. Therefore, 2~3 KPa error caused by 20~30 cm water head has very significant influence on the air entry value test.

3. It is impossible terminate the sampling test in the process of the soil water characteristic hysteresis curve test of unsaturated soil. Therefore, the initial soil samples are required to be in saturated state. The soil samples are traditionally saturated usually using outdoor pressure head or back pressure, and then tested in a pressure chamber. But any method has the problem of disturbing soil samples in handling, and saturated original soil samples tend to be slightly liquefied due to shock, so that some of the original interspaces turn smaller, thereby changing the structural style of the undisturbed soil, affecting precise air entry value test of the soil mass, and changing the shape of the soil water characteristic curve of undisturbed soil.

Therefore, developing a device that allows soil samples to be in a state of zero water pressure gradient in the process of dehydration and soaking, and is capable of vacuum saturation of the test samples directly in the pressure chamber has important significance for accurate determination of hysteresis problems of soil water characteristic curve of unsaturated soil.

SUMMARY OF THE INVENTION

In view of the prior art described above, the present invention aims to provide a device for simply and accurately determining soil-water characteristics of unsaturated soil, so as to solve at least one of the defects in the prior art.

In order to achieve the purpose of the present invention, the present invention provides the technical solutions as follows:

A test device, comprising a closeable cavity and a water flow groove with a water transmission channel therebetween, wherein the water flow groove is below the cavity, and the water flow groove comprises a water inlet and a water outlet, the depth of the water inlet is greater than the depth of the water outlet.

Preferably, the water flow groove is extending bent.

Preferably, the water flow groove is helical-shaped from a top view.

Preferably, the water flow groove is an equally spaced helix.

Preferably, the depth of the water flow groove is linearly decreased from the water inlet to the water outlet.

Preferably, the water flow groove is formed by a blocky base with the upper surface concaving downward.

Preferably, a vertical drum is arranged on the upper surface of the base, the upper end face of the vertical drum is covered with a cover plate, the cover plate, drum and base are enclosed to form a cavity.

Preferably, a stud extends upward from the upper surface of the base. The stud passes through the cover plate, and is then locked by a nut, so that the cover plate is clung onto the drum on the upper surface of the base.

Preferably, an air hole is configured on the cover plate.

Preferably, the air hole is connected with an air circulation channel, and an air flow control valve is configured on the air circulation channel.

Preferably, the upper surface central area of the base integrally concaving downward, in order to form a shallow groove used to accommodate a ceramic plate. The water flow groove is located below the shallow groove.

Preferably, at least a part of the shallow groove extends to below the side wall of the drum, so that the side wall of the drum is able to define the ceramic plate.

Preferably, the circumference of the ceramic plate is bonded with a protective steel ring.

Preferably, at least a part of the protective steel ring is located below the side wall of the drum, so that the side wall of the drum is able to define the protective steel ring and ceramic plate.

Preferably, the outer circumference of the protective steel ring and the side wall of the shallow groove are sealed with an O-ring.

Preferably, the water inlet is connected with the end of a vertical water inlet pipe, a sealing rubber plug is configured on the top end of the water inlet pipe, a bent pipe opening to the atmosphere is configured on the side wall of the water inlet pipe, the bent pipe is higher than the upper surface of the water flow groove, and the height difference between the bent pipe and the water flow groove is at least equal to the height of the ceramic plate used to be placed above the water flow groove.

Preferably, the end of the bent pipe is a funnel structure opening upward.

Preferably, a water inlet control valve is configured between the water inlet pipe and the water inlet.

Preferably, the water inlet pipe capable of adjusting height is configure on a cross rod of a cross-shaped stand.

Preferably, the water outlet is connected to the side wall of a drain pipe, the drain port of the drain pipe connected with the water outlet is higher than the upper surface of the water flow groove, and the height difference between the drain port and the water flow groove is at least equal to the height of the ceramic plate used to be placed above the water flow groove.

Preferably, the drain port is a declivitous and small pipe.

Preferably, the angle of intersection between the drain port and the drain pipe is 80°.

Preferably, the drain port is 10 cm from the upper end of the drain pipe.

Preferably, the upper end of the drain pipe is a necking structure with reducing inner diameter.

Preferably, the drain pipe capable of adjusting height is arranged on a cross rod of another cross-shaped stand.

In the present invention, the water inlet is located at high place, while the water outlet is located at low place. In application, the bubbles generated due to bottom migration of the ceramic plate are collected in the groove, come up due to the buoyancy effect, and are then discharged via the water outlet, so as to not only avoid the cumbersome operation steps of repeated washing, but also ensure that there is not water pressure at the bottom of the ceramic plate in the air entry value test process, and improve the control accuracy of the soil matrix suction.

EMBODIMENT OF THE PRESENT INVENTION

The present invention is further illustrated in detail in the light of the drawings and embodiments as follows.

Figure 1:
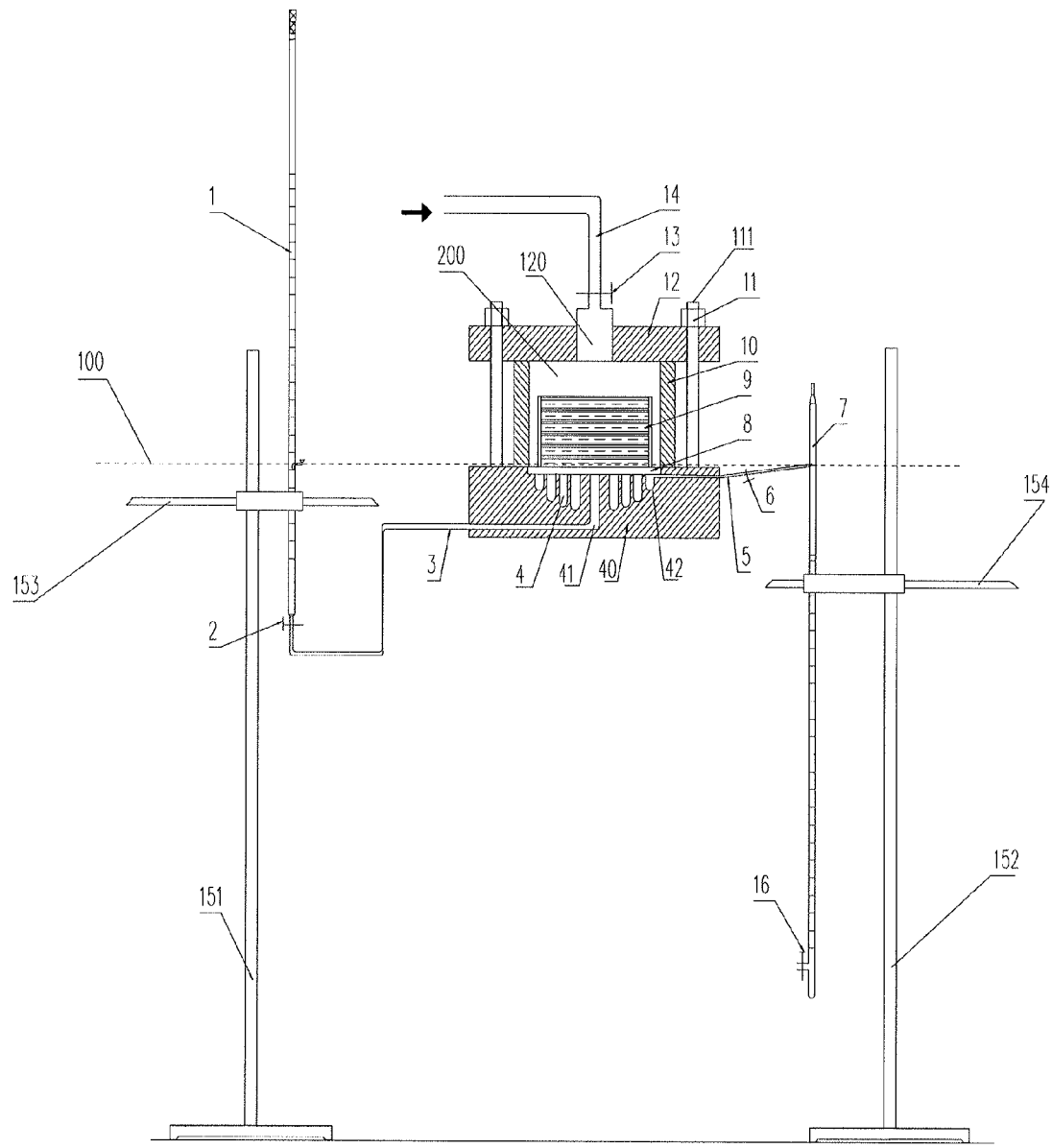
FIG. 1 is the structure diagram of the embodiment in the present invention (base etc. as shown in the section view)
Figure 2:
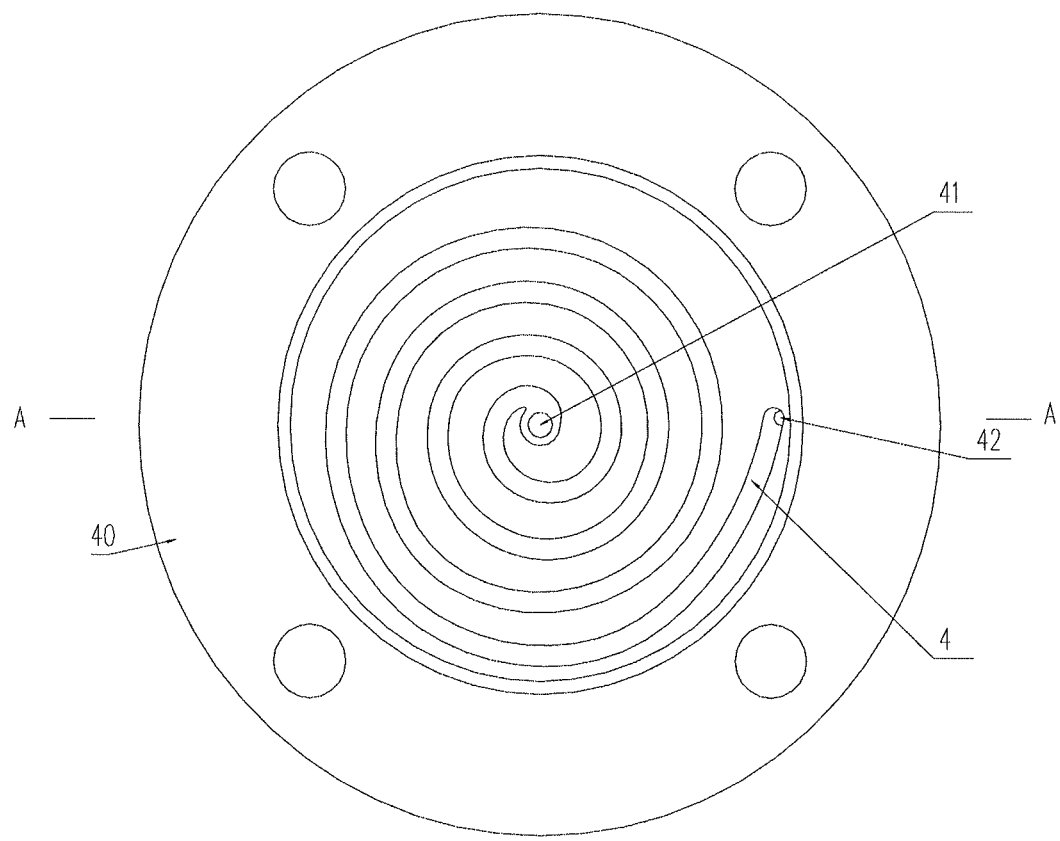
FIG. 2 is the top view of the base structure of the embodiment in the present invention.
Figure 3:
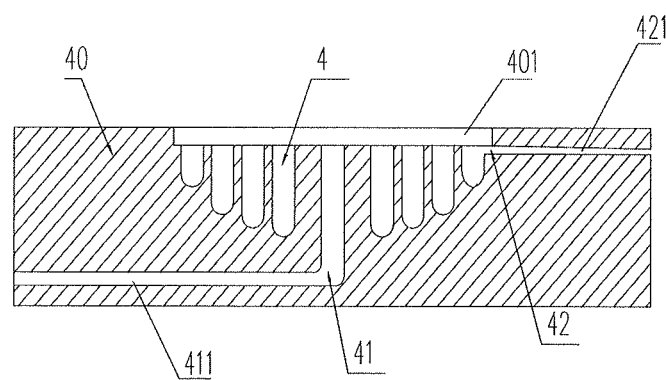
FIG. 3 is the section view along with A-A line displayed in FIG. 2 of the embodiment in the present invention.

As shown in FIG. 1, FIG. 2 and FIG. 3, the embodiment of the present invention comprises a closeable cavity 200 (used as a pressure chamber) and a water flow groove 4, wherein the cavity 200 can not only be closed, but also be opening to the outside air, and the internal space therein is used to accommodate soil sample 9 to test the characteristics of unsaturated soil. The water flow groove 4 below the cavity 200 is used to deliver water to the soil sample 9. There is a water transmission channel between the water flow groove 4 and the cavity 200, such as the ceramic plate 8 exists between the cavity 200 and the water flow groove 4. The water flow groove 4 comprises a water inlet 41 and a water outlet 42, where the water inlet 41 is deeper than the water outlet 42. That is, in FIG. 1 and FIG. 3, the height of the water outlet 42 is greater than the height of the water inlet 41. In the dehumidification curve test of the soil sample 9 according to the embodiment according to the present invention, the position of water outlet 42 is higher than the position of the water inlet 41, and the bubbles occurred from the water flow groove 4 located at the bottom of the ceramic plate 8 due to the migration are discharged into the drain pipe 7 through the outlet connecting pipe 5 based on the buoyancy effect, and the existence of the bubbles in the test processing does not influence water drainage amount measured, so as to not only avoid the cumbersome operation steps of repeated washing, but also improve the accuracy of water drainage amount measured.

As shown in FIG. 2, the water flow groove 4 in the embodiment according to the present invention is extending bent, and non-linear extension design thereof can not only increase the effective drainage area of the ceramic plate 8, but also guarantee the loading capacity of the ceramic plate 8. Furthermore, overlooking water flow groove 4 is helical-shaped from top view thereof in an overlooking. As shown in FIG. 1 and FIG. 3, the water flow groove 4 is an equally spaced helix, meaning that, adjacent grooves in FIG. 3 are substantially equally spaced.

In the embodiment of present invention, both FIG. 1 and FIG. 3 show the depth changes of the water flow groove 4, that is, depth of the water flow groove 4 is smoothly and linearly decreased from the water inlet 41 to the water outlet 42, i.e. beginning from the water inlet 41, the bottom of the water flow groove 4 is gradually raised, and the changes therein are substantially linear.

As shown in FIG. 1 and FIG. 3, the water flow groove 4 is formed by the upper surface of a blocky-shaped base 40 concaving downward. Accordingly, an inlet channel 411 horizontally extending used to connect with water inlet 41 opening to the outside is configured on the base 40, as well as an outlet channel 421 used to connect with the water outlet 42 opening to the outside, so that the water inlet 41 and water outlet 42 of the water flow groove 4 are respectively connected with the inlet connecting pipe 3 and outlet connecting pipe 5. Preferably, the top of the outlet channel 421 clings to the lower surface of the ceramic plate 8. As shown in FIG. 1, a vertical drum 10 is arranged on the upper surface of the base 40, such as a cylinder-shaped drum, forming the side face of the cavity 200. The cover plate 12, drum 10 and base 40 may become an integral structure by studs 11 to form the cavity 200.

In order to fix and seal the cover plate 12 onto the drum 10, a stud 11 extending upward is configured on the upper surface of the base 40, i.e. the lower end of the stud 11 is fixed on the base 40, multiple studs are necessary and the studs 11 are uniformly distributed on the outer side of the drum 10. The upper end of the stud 11 passes through the cover plate 12, and is then tightly locked by the nut 111 in order to make the cover plate 12 compacting the drum 10 onto the upper surface of the base 40.

As shown in FIG. 1, an air hole 120 is configured on the cover plate 12 in order to realize ventilation of the cavity 200 with outside air, the air hole 120 is also connected to an air circulation channel, such as an air pipe 14, and an air flow control valve 13 is configured on the air pipe 14 in order to realize free control of the ventilation of the cavity 200 with the outside air.

Figure 6:
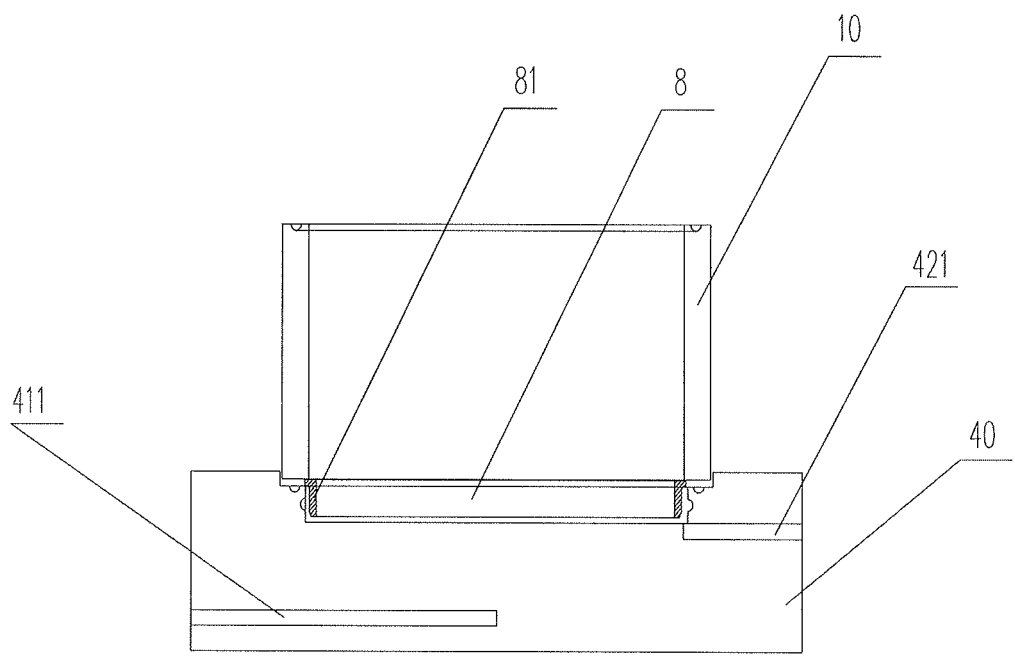
FIG. 6 is the detailed structure diagram of soil samples, ceramic plate and base of the embodiment in the present invention.

At least in order to accurately define the position of the ceramic plate 8, as shown in FIG. 3, the upper surface central area of the base integrally concaving downward to form a shallow groove 401 used to accommodate the ceramic plate 8, and the whole water flow groove 4 is located below the shallow groove 401. Furthermore, at least a part of the shallow groove 401 extends to below the side wall of the drum 10, so that the side wall of the drum 10 can be pressed at the edge of the ceramic plate 8 embedded in the shallow groove 401 to define the position of the ceramic plate 8. More preferably, as shown in FIG. 6, the circumference of the ceramic plate 8 is bonded with a protective steel ring 81, for example is bonded through epoxy resin, in order to prevent edge damage of the ceramic plate 8. Thus, it is also possible to allow at least a part of the protective steel ring 81 (such as its edge) to be located below the side wall of the drum 10, so as to avoid directly pressing the edge of the ceramic plate 8 to below the side wall of the drum 10. Furthermore, the outer circumference of the protective steel ring and the side wall of the shallow groove 401 are sealed using an O-ring (the arc-shaped groove in FIG. 6 is used for the O-ring to be embedded in), in order to further increase the sealing effect of the cavity 200.

Figure 4:
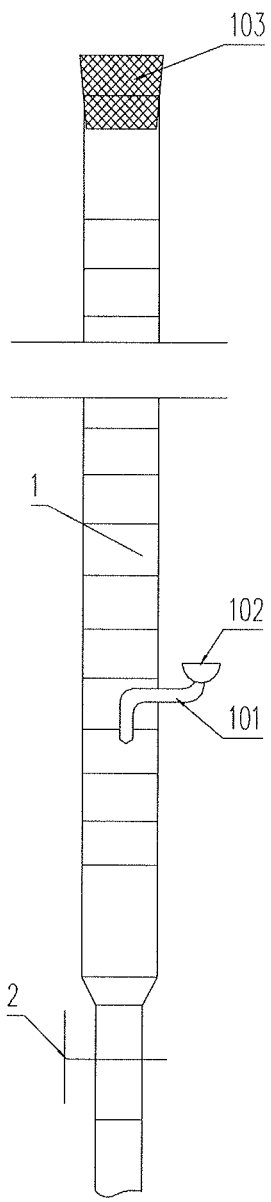
FIG. 4 is the structure diagram of the water inlet pipe of the embodiment in the present invention.

As shown in FIG. 1, the inlet channel 411 is connected with the end of the vertical water inlet pipe 1 through an water inlet connecting pipe 3 and an water inlet control valve 2 arranged on the water inlet connecting pipe 3. As shown in FIG. 1 and FIG. 4, a sealing rubber plug 103 is arranged on the top of the water inlet pipe 1, a bent pipe is configured on the side wall of the water inlet pipe 1 opening to the atmosphere, the bent pipe 101 is higher than the upper surface of the water flow groove 4, and the height difference between the bent pipe 101 and the water flow groove 4 is at least equal to the height of the ceramic plate 8 used to be placed above the water flow groove 4. As shown in FIG. 1, the dotted line 100 is equal to the height of the upper surface of the ceramic plate 8, and the height of the bent pipe 101 is equal to the height of the dotted line 100.

The bent pipe 101 with equal height to the ceramic plate 8 and connected with the outside can realize water supplement of the soil sample 9 at a constant water level. In conventional soaking experiment, there will be excess water on the upper surface of the ceramic plate 8 at low matrix suction due to water supplemental faucet being at higher position, thereby the test's accuracy will be influenced. This embodiment realizes water supplement to constant water level in the whole soaking experimental process, thereby greatly improving the soaking curve test precision of unsaturated soil.

The water inlet pipe 1 (improved Mariotte flask) is not affected by temperature and air pressure, and has the advantage of low measurement error. Therefore, in order to facilitate adjusting the water volume in the water inlet pipe 1 and bent pipe 101, the end of the bent pipe 101 is a funnel structure 102 opening upward, as shown in FIG. 1. When the indoor air temperature and air pressure change, water will overflow from the bent pipe 101 of the traditional Mariotte flask. In this embodiment, an open funnel structure 102 is arranged at the outlet of the bent pipe 101 to store the overflow water caused by changing outside conditions, so as to realize the water flow rate adjustment, and improve the water inflow test precision.

When this embodiment is assembled, it may be necessary to adjust the height of the water inlet pipe 1. Therefore, the water inlet pipe 1 of the embodiment is fixed on a cross rod 153 of a cross-shaped bench 151, where, height of the cross rod 153 is adjustable. Similarly, the drain pipe 7 hereinafter is also arranged on a cross rod 154 of a cross-shaped bench 152.

Figure 5:
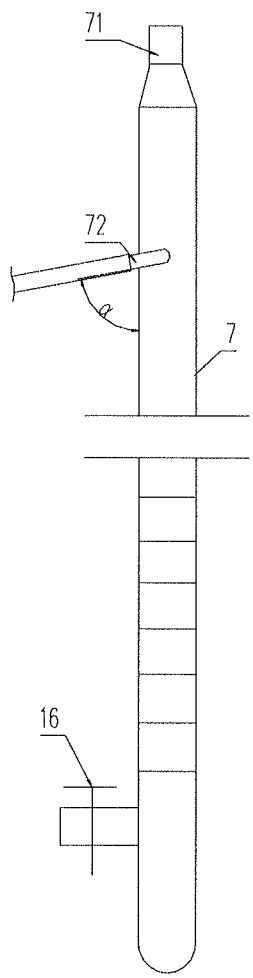
FIG. 5 is the structure diagram of the drain pipe of the embodiment in the present invention.

As shown in FIG. 5, the water outlet 42 of this embodiment is connected with the side wall of the drain pipe 7 through an outlet channel 421, an outlet connection pipe 5, and an outlet control valve 6 installed on the outlet connection pipe 5. Besides, graduation is also provided on the surface of the drain pipe 7. In the same way, graduation is also provided on the surface of the foregoing water inlet pipe 1, so as to facilitate promptly reading the water level data therein. A drain control valve 16 is installed at the lower end of the drain pipe 7. Drain port 72 of the drain pipe 7 connected to the outlet connection pipe 5 is higher than the upper surface of the water flow groove 4, and the height difference between the drain port 72 and the water flow groove 4 is at least equal to the height of the ceramic plate 8 used to be placed above the water flow groove 4, that is, height of the drain port 72 is equivalent to the dotted line 100.

Height of the laterally introducing drain port 72 of the drain pipe 7 is equal to the dotted line 100, which has the same effect as the situation that the bent pipe 101 on the side wall of the water inlet pipe 1 with fixed water head has consistent height with the top surface of the ceramic plate 101, so that the soil sample 9 under test has zero water gradient in the process of dehydration and soaking, thereby ensuring the accuracy of the test results.

Preferably, the drain port 72 is a declivitous tubule, and is about 10 cm from the upper end of the drain pipe 7. Furthermore, there is an angle $\alpha$ of 80 degrees between the tubule and the drain pipe 7. Inclined design of the drain port 72 not only facilitates smooth water discharge, but also avoids the air flow back into the base 40.

More preferably, the upper end of the drain pipe 7 is a throat structure 71 with reducing inner diameter. The throat design is used to reduce water evaporation in the drain pipe 7 and reduce the measurement errors.

In this document, the term "soil water characteristic curve" is used to reflect the relationship between the matrix suction and volumetric water content.

In conclusion, the drain pipe 7 in this embodiment has improved the design of the existing "pressure-bearing" drain pipe, and can realize "no water pressure", so that in the entire drainage experiment process of unsaturated soil, water pressure below the ceramic plate 8 is zero, so as to solve the problem of water pressure changes in the traditional test method, and improve the accuracy of the air entry value test.

According to this embodiment, the hysteresis curve of unsaturated soil may be determined by referring to the following operation steps:

I. Preparation.

The water inlet pipe 1 with fixed water head is fixed on the bench 15 in such a way that the bent pipe 101 on the side wall of the water inlet pipe 1 is guaranteed to be 1 cm higher than bottom surface center of the soil sample 9 (namely top surface of the ceramic plate 8) (height of the dotted line 100).

The water inlet connecting pipe 3 is connected with the water inlet pipe 1, and the water inlet control valve 2 is switched off. The water inlet pipe 1 is filled with water, and then sealed with a sealing rubber plug 103.

The drain pipe 7 is fixed on the bench 15 in such a way that the height of the drain port 72 is guaranteed to be consistent with that of the top surface of the ceramic plate 8. The drain port 72 is connected to the outlet connection pipe 5.

The water inlet control valve 2 is switched on, and the water flows out of the outlet connection pipe 5 through the water flow groove 4. After excess gas is removed and stable water flow is formed, the water inlet control valve 2 is switched off, the outlet control valve 6 is switched off, and the drainage control valve 16 is switched on to remove excess water until the water level is reasonable.

II. Vacuum Saturation of the Soil Sample.

The soil sample 9 (with a cutting ring) is placed in a pressure chamber cavity 200, covered with a cover plate 12, and locked with nuts 111 and studs 11 to realize sealing and fixation of the cavity 200.

The water inlet control valve 2 and outlet control valve 6 are shut off. The air pipe 14 is connected to the vacuum pump to extract air until one negative atmospheric pressure for an hour.

The water inlet control valve 2 is switched on, so that water flows into the water flow groove 4 from the water inlet pipe 1, and enters the soil sample 9 via the ceramic plate 8 based on the upper and lower water pressure difference (note that it is necessary to promptly supplement water to the water inlet pipe 1 in this process), where the water inflow is recorded.

When the water inflow is more than 1.4 times that of the pore volume of the soil sample 9, the water inlet control valve 2 is switched off to stop air extraction. After left to stand for an hour, the pressure chamber freely introduces air.

The air pipe 14 is connected to the air source. After applying 2 kPa air pressure, the outlet control valve 6 is switched on to observe the water level of the drain pipe 7. If it is stable, it shows that excess water is completely discharged from the cavity 200, and the soil sample 9 is saturated.

III. Drainage Experiment.

The water inlet control valve 2 is kept open, and the outlet control valve 6 is kept in off state for 1~2 days, in order to fully saturate the ceramic plate 8 and soil sample 9.

The water inlet control valve 2 is kept in off state, and the outlet control valve 6 is kept open for 1 day, in order to allow excess water to flow out of the cavity 200.

After adjusting the given air pressure, the air control valve 13 is switched on to apply matrix suction to the soil sample 9. After the drainage is stable, the water discharge is read and recorded by the graduation of the drain pipe 7, and then the pressure is increased to the next measurement level generally according to the following law: 2, 3, 4, 5, 6, 8, 10, 15, 20, 30, 50, 100, 250, 500 (kPa). The pressure is slowly increased at the initial stage to test the air entry value of the soil mass.

IV. Soaking Experiment.

After the drainage experiment, the air pressure is kept constant, and the water inlet control valve 2 is switched on to wash the base 4. Afterwards, the outlet control valve 6 is switched off, and the water inlet control valve 2 is switched off.

The sealing rubber plug 103 at the upper end of the water inlet pipe 1 is switched on, water is injected to the maximum graduation, and the sealing rubber plug 103 is covered. The water inlet control valve 2 is switched on and is kept open for 3 hours.

The air pressure is reduced step by step. At all levels of air pressure, after soaking is stable, the water soaking amount at the air pressure level is read and recorded by the graduation of the water inlet pipe 1 under the prerequisite that the indoor air pressure and air temperature are guaranteed constant.

It is possible to accurately calculate the hysteresis curve of unsaturated soil using the data obtained from the above drainage experiment and soaking experiment.

In conclusion, the water outlet of the water flow groove in the present invention is high, while the water inlet thereof is low. In the test, bubbles are generated in the water flow groove, come up due to the buoyancy effect, and are discharged from the high water outlet. The discharged bubbles are discharged from the upper outlet of the drain pipe, and do not enter water in the drain pipe, so to avoid the influence of air on the test results. Automatic discharge of bubbles also avoids the cumbersome operation steps of repeated washing.

In the present invention, optimization design of the water inlet pipe aims to provide a bent pipe opening to the atmosphere on the side wall, and guarantee constant inlet pressure. In order to avoid overflow of water when the indoor air temperature and air pressure change, outlet of the bent pipe is equipped with an open funnel structure, so as to store the overflow water caused by changing outside conditions, and improve the accuracy of water inflow test.

The lateral induction pipe of the drain pipe and bent pipe on the side wall of the water inlet pipe are as high as the top surface of the ceramic plate, so that the water pressure gradient of the soil sample under test is zero in the process of dehydration and soaking, thereby guaranteeing the accuracy of the test results.

Throat design is used for the mouth of the drain pipe, which can reduce water evaporation in the drain pipe and reduce the measurement error; the lateral induction pipe is inclinedly connected to the drain pipe, which can not only facilitate smooth water discharge, but also avoid the air flow back into the base.

The inner diameter of the drum is less than the steel ring design on the outer side of the ceramic plate, so that the test device is capable of vacuum saturation inside the cavity, thereby avoiding the test sample disturbance problem caused by external saturation.

In conclusion, the present invention provides an unsaturated soil test device with good operability, which can not only ensure the reliability of the test results, but also avoid the cumbersome steps of repeated washing to discharge bubbles.

Obviously, those skilled in the art may alter and modify the embodiments in the present invention in various forms without departing from the spirit and scope of the embodiments in the present invention. In this way, if these alterations and modifications of the embodiments in the present invention fall within the scope of the claims of the present invention and its equivalent technology, the present invention is also intended to include these alterations and modifications.

The invention claimed is:

1. A test device comprising a closeable cavity and a water flow groove with a water transmission channel therebetween, the water flow groove is located below the cavity, and the water flow groove comprises a water inlet and a water outlet, the depth of the water inlet is greater than the depth of the water outlet;
the water flow groove is extending bent, the water flow groove is helical-shaped from a top view, the water flow groove is an equally spaced helix; the depth of the water flow groove is linearly decreased from the water inlet to the water outlet; the water flow groove is formed by a blocky base with the upper surface concaving downward;
a vertical drum is arranged on the upper surface of the base, the upper end face of the vertical drum is covered with a cover plate, the cover plate, drum and base are enclosed to form a cavity; an air hole is configured on the cover plate.

2. The test device according to claim 1, wherein: a stud extends upward from the upper surface of the base, the stud passes through the cover plate, and is then locked by a nut, so that the cover plate is clung onto the drum on the upper surface of the base.

3. The test device according to claim 1, wherein: the air hole is connected with an air circulation channel, and an air flow control valve is configured on the air circulation channel.

4. The test device according to claim 1, wherein: the upper surface central area of the base integrally concaving downward, in order to form a shallow groove used to accommodate a ceramic plate, the water flow groove is located below the shallow groove.

5. The test device according to claim 4 wherein: at least a part of the shallow groove extends to below the side wall of the drum, so that the side wall of the drum is able to define the ceramic plate.

6. The test device according to claim 4 wherein: the circumference of the ceramic plate is bonded with a protective steel ring.

7. The test device according to claim 6, wherein: at least a part of the protective steel ring is located below the side wall of the drum, so that the side wall of the drum is able to define the protective steel ring and ceramic plate.

8. The test device according to claim 6, wherein: the outer circumference of the protective steel ring and the side wall of the shallow groove are sealed using an O-ring.

9. The test device according to claim 1, wherein: the water inlet is connected with the end of a vertical water inlet pipe, a sealing rubber plug is configured on the top end of the water inlet pipe, a bent pipe opening to the atmosphere is configured on the side wall of the water inlet pipe, the bent pipe is higher than the upper surface of the water flow groove, and the height difference between the bent pipe and the water flow groove is at least equal to the height of the ceramic plate used to be placed above the water flow groove.

10. The test device according to claim 9, wherein: the end of the bent pipe is a funnel structure opening upward.

11. The test device according to claim 9, wherein: an inlet control valve is configured between the water inlet pipe and the water inlet.

12. The test device according to claim 9, wherein: the water inlet pipe capable of adjusting height is configure on a cross rod of a cross-shaped stand.

13. The test device according to claim 1, wherein: the water outlet is connected to the side wall of a drain pipe, the drain port of the drain pipe connected with the water outlet is higher than the upper surface of the water flow groove, and the height difference between the drain port and the water flow groove is at least equal to the height of the ceramic plate used to be placed above the water flow groove.

14. The test device according to claim 13, wherein: the drain port is a declivitous and thin pipe.

15. The test device according to claim 14, wherein: the angle of intersection between the drain port and the drain pipe is 80°.

16. The test device according to claim 13, wherein: the drain port is 10 cm from the upper end of the drain pipe.

17. The test device according to claim 13, wherein: the upper end of the drain pipe is a end-shrinked structure with reducing inner diameter.

18. The test device according to claim 13, wherein: the drain pipe capable of adjusting height is arranged on a cross rod of another cross-shaped stand.

* * * * *